US012611527B2

(12) United States Patent
Stöver et al.

(10) Patent No.: US 12,611,527 B2
(45) Date of Patent: Apr. 28, 2026

(54) CATHETER WITH A BALLOON AND A SEPARATE INFLATION LUMEN

(71) Applicant: SMD Swiss Medical Devices AG, Beringen (CH)

(72) Inventors: Michael Stöver, Fruthwilen (CH); Fabian Eckermann, Jona (CH); Willi Zwahlen, Betschdorf (FR)

(73) Assignee: SMD Swiss Medical Devices AG, Beringen (CH)

( * ) Notice: Subject to any disclaimer, the term of this patent is extended or adjusted under 35 U.S.C. 154(b) by 1010 days.

(21) Appl. No.: 17/433,478

(22) PCT Filed: Feb. 4, 2020

(86) PCT No.: PCT/EP2020/052748
§ 371 (c)(1),
(2) Date: Aug. 24, 2021

(87) PCT Pub. No.: WO2020/173676
PCT Pub. Date: Sep. 3, 2020

(65) Prior Publication Data
US 2022/0134064 A1 May 5, 2022

(30) Foreign Application Priority Data
Feb. 28, 2019 (EP) ..................................... 19159998

(51) Int. Cl.
*A61M 25/10* (2013.01)
*A61M 25/00* (2006.01)
*A61M 29/02* (2006.01)

(52) U.S. Cl.
CPC .... *A61M 25/1036* (2013.01); *A61M 25/0032* (2013.01); *A61M 25/1034* (2013.01);
(Continued)

(58) Field of Classification Search
CPC .. A61M 2025/0059; A61M 2025/0183; A61M 2025/1056; A61M 2025/1061;
(Continued)

(56) References Cited

U.S. PATENT DOCUMENTS 5,415,634 A * 5/1995 Glynn ............ A61B 17/320783
604/103.08
5,484,449 A * 1/1996 Amundson ............. A61F 2/958
606/198
(Continued)

FOREIGN PATENT DOCUMENTS

FR 2996774 A1 4/2014

OTHER PUBLICATIONS

Extended European Search Report from the European Patent Office dated Aug. 29, 2019 in related EP application No. 19 159 998.4, including Search Report and Search Opinion.
(Continued)

*Primary Examiner* — Mohamed G Gabr
(74) *Attorney, Agent, or Firm* — Tucker Ellis LLP

(57) ABSTRACT

A catheter (1) includes an elongated member (2) having a proximal end (4) and a distal end (3). An inflatable balloon (5) is arranged on the elongated member in an area of the distal end thereof, the balloon extending from a distal position (6) to a proximal position (7). The elongated member includes an inner lumen (8) extending from the distal end to an end position (9) which is proximal to the balloon. The inner lumen is open at the distal end. The catheter further includes a duct (12) connected to the proximal end and to the balloon at the proximal position. The duct defines a separate lumen to convey a fluid to and from the balloon.

20 Claims, 2 Drawing Sheets

(52) U.S. Cl.
CPC ..... *A61M 29/02* (2013.01); *A61M 2025/1056*
(2013.01); *A61M 2025/1061* (2013.01)

(58) Field of Classification Search
CPC .......... A61M 25/0032; A61M 25/1034; A61M
25/1036; A61M 25/104
See application file for complete search history.

(56) References Cited

U.S. PATENT DOCUMENTS

| | | | |
|---|---|---|---|
| 5,516,336 A | | 5/1996 | McInnes et al. |
| 5,649,909 A | * | 7/1997 | Cornelius ......... A61M 25/0045 604/96.01 |
| 5,728,063 A | * | 3/1998 | Preissman ......... A61M 25/0054 604/103.09 |
| 5,947,925 A | * | 9/1999 | Ashiya .............. A61M 25/0169 604/164.08 |
| 2007/0073269 A1 | | 3/2007 | Becker |
| 2010/0312101 A1 | * | 12/2010 | Drontle .................. A61B 17/24 606/196 |

OTHER PUBLICATIONS

International Search Report and Written Opinion of the International Searching Authority dated Apr. 14, 2020 in parent PCT application No. PCT/EP2020/052748.

* cited by examiner

Fig. 2b                    Fig. 2a

CATHETER WITH A BALLOON AND A SEPARATE INFLATION LUMEN

CROSS-REFERENCE

This application is the U.S. National Stage of International Application No. PCT/EP2020/052748 filed on Feb. 4, 2020, which claims priority to European Patent Application No. 19159998.4 filed on Feb. 28, 2019.

TECHNICAL FIELD

The invention relates to a catheter with a balloon which may be produced with a minimal amount of manufacturing steps and number of parts as well as a method for manufacturing such a catheter.

BACKGROUND ART

Catheters as known in the art usually comprise an inflatable balloon arranged at a distal end of the catheter as well as a stiffer hypotube used to push the catheter through a body vessel of a patient. Further, such a catheter comprises a lumen for a fluid used to inflate the balloon as well as a lumen through which a guide wire may be inserted. The guide wire lumen remains open at a distal end of the catheter. The guide wire lumen may stretch through the entire catheter such that the guide wire may pass through the entire catheter (so-called over the wire catheter) or an exit port may be provided at a position proximal to the balloon such that the guide wire may exit the catheter via said exit port (so-called rapid exchange or monorail catheter).

Catheters as known in the art are typically assembled from six or more different parts in up to forty manual assembly steps. This leads to high production costs, especially since each assembly step requires appropriate quality control.

The parts include tubes providing the lumen for the inflation fluid as well as the guide wire lumen, the hypotube, the balloon and the guide wire exit port as well as an adapter located at a proximal end of the catheter.

Rapid exchange catheters, which are also known as monorail catheters, usually comprise a guide wire lumen which is located within an inflation lumen of the catheter. Said guide wire lumen exits the inflation lumen via an opening. In order to connect the guide wire lumen with the opening in a fluid tight manner, a welding seam is necessary.

SUMMARY OF THE INVENTION

It is the object of the invention to create a balloon catheter which is composed of a minimum number of parts and which may be produced by a minimal number of assembly steps.

In one aspect of the present teachings, the catheter may comprise an elongated member having a proximal end and a distal end. An inflatable balloon is arranged on said elongated member in an area of the distal end thereof, the balloon extending from a distal position to a proximal position. The elongated member comprises an inner lumen extending from the distal end to an end position which is proximal to the balloon. The inner lumen is open at the distal end. The catheter further comprises a duct connected to the proximal end and to the balloon at the proximal position, said duct defining a separate lumen to convey a fluid to and from the balloon.

The catheter according to the present invention only comprises a few parts which may be manufactured with only a minimum of assembly steps. This greatly reduces the costs for manufacturing such a catheter. Further, the parts needed for the inventive catheter are simple to produce, hence further decreasing the manufacturing costs of the catheter.

The catheter according to the present invention is preferably used in percutaneous transluminal angioplasty (PTA) procedures, especially percutaneous transluminal coronary angioplasty procedures (PTCA). The balloon is thereby preferably used to widen a narrowed or obstructed artery or vein. Further, in alternative embodiments, the balloon may also be used to expand a stent mounted on the balloon.

In the present application, the term "proximal end" means the end of the catheter which remains outside of a patient during a procedure. I.e. the proximal end is the end of the catheter pointing away of a treatment site, typically a narrowed or obstructed stretch of an artery or vein, during the procedure. Concurrently, the "distal end" is the end of the catheter which is introduced into a blood vessel of a patient to be treated. I.e. the distal end is the end of the catheter which will be positioned at the treatment site.

In the present application, the term "separate lumen" is understood to mean a lumen which is only punctually connected to the elongated member. This means that the duct is only punctually connected to the elongated member. I.e. the duct remains unconnected to the elongated member for most of its length. Preferably, the duct and hence the separate lumen is only connected to the elongated member at the proximal end and to the balloon at the proximal position. With the exception of these two connection points, the duct and hence the separate lumen is preferably not connected with the elongated member. The elongated member is made of at least one material which has a sufficient flexibility to allow the introduction and passage of the catheter through body vessels, specifically through blood vessels of a patient. Preferably, the elongated member comprises at least one polymer material, at least one metal or at least one metal alloy, or a combination thereof.

The elongated member is preferably in the form of a hollow tube at least in the area comprising the inner lumen, i.e. between said distal end and the end position. The hollow tube has a circumferential wall. The thickness of the circumferential wall is thereby selected such that the hollow tube may bend easily without that the inner lumen collapses. The elongated member preferably has a round cross section. The elongated member preferably has a diameter of 0.2-1.2 mm, preferably of 0.4-0.6 mm.

The inner lumen is open at the distal end such that a guide wire may be introduced into said inner lumen through this opening. Hence, the inner lumen serves the function of guidewire lumen.

Typically, in a PTA procedure, a guide wire is introduced first into a patient such that the guide wire spans through blood vessels from an incision area to the treatment site and unusually a short distance past said treatment site. A proximal end of the guide wire is then introduced into the inner lumen at the distal end of the catheter and the catheter is subsequently pushed over the guide wire until the distal end of the catheter reaches the treatment site.

Preferably, the balloon is located a first distance from the distal end of the catheter. Hence, the catheter comprises a distal tip spanning from the distal end of the catheter to the balloon. Preferably, a hydrophilic coating is applied on the outer surface of the elongated member in the area of said distal tip. Preferably the first distance and hence the length of the distal tip is from 1 mm to 4 mm.

The balloon has a length which may vary depending on the intended use of the catheter. Preferably, the balloon has a length from 4 mm to 35 mm. The balloon spans from a distal position to a proximal position, wherein the length of the balloon equals the distance between said distal position and said proximal position.

The balloon preferably has a round cross-section with a diameter in the expanded state of preferably from 1 mm to 6 mm, more preferably from 1.5 mm to 4.5 mm. The balloon is preferably made of a polymer material and the wall thickness of the balloon material is chosen such that the balloon may withstand pressures of 10 bar to 40 bar. In the area of the distal position and of the proximal position the balloon preferably has conical sections where the diameter of the balloon is reduced to the diameter of the elongated member. The balloon may be formed by methods known in the art, e.g. by blow moulding.

The balloon encircles the elongated member. This means that the elongated member is arranged within a volume of said balloon between the distal position and the proximal position. The balloon is connected to the elongated member by a fluid-tight connection. Preferably the balloon is connected by means of welding or by means of an adhesive.

Preferably, the balloon is provided in a collapsed configuration and may be inflated by the introduction of a fluid, especially of a liquid, under pressure from the collapsed configuration into an inflated configuration. The at least one separate lumen is thereby preferably used as inflation lumen which conveys the fluid towards and from the balloon. Therefore, the separate lumen is thereby fluidly connected to the volume of the balloon in order to allow a fluid exchange between the separate lumen and the volume of the balloon.

Preferably, the end position and the proximal position of the balloon are spaced from each other by a second distance. In one embodiment, the end position may be located at the proximal end of the catheter. In this case, the inner lumen would extend from the distal end to the proximal end of the catheter. Hence, a guidewire may be advanced from the distal end to the proximal end along the entire length of the elongated member. In this configuration, the catheter can be used as so-called over-the-wire catheter.

However, preferably, the end position is located distal to the proximal end. In this case, the inner lumen does not extend along the entire length of the catheter, i.e. along the entire distance between the distal end and the proximal end. In this case, it is preferable to provide an access port for the passage of a guide wire from the inner lumen to the outside of the catheter in the area of the end position.

Preferably, the duct is connected to the elongated member only at the proximal end and at the proximal position. Between these two connection points, the duct remains free, i.e. unconnected to the elongated body.

Preferably, the duct is freely spirally wound around the elongated member. This allows keeping the duct close to the elongated member while still allowing a free movement of the duct relative to the elongated member, for example when the catheter is passed through a tight turn of a body vessel.

The number of windings of the duct around the elongated member may vary depending on the length of the elongated member, i.e. the distance between the proximal end and the distal end as well as on the length of the duct.

The duct preferably has a cross section in the form of an oval or circle. More preferably, said duct has a cross section in the form of an ellipse. An oval is understood herein to mean a geometric circle that is flattened to an egg like shape. A special form of an ellipse is a stadium which is a two-dimensional geometric shape constructed of a rectangle with semicircles at a pair of opposite sides.

The use of a duct with such a cross-section has the advantage that the separate lumen has a sound cross-section surface while the dimension of the duct in one direction may be kept minimal when compared to a round cross-section with a comparable cross-section surface. Further, a cross-section in the form of an oval or ellipse also has the advantage that the separate lumen is less likely to collapse over the entire surface when an underpressure is applied in order to deflate the balloon.

Alternatively, the duct may have a cross-section in the form of a crescent. In this case, the inner convex curvature of the crescent is preferably oriented towards the elongated member and has substantially the same radius of curvature as the elongated member.

Preferably, the duct comprises at least one support element being arranged longitudinally along a length of said duct within said separate lumen. The support element reduces the risk that the separate lumen collapses when an underpressure is applied in order to withdraw fluid to deflate the balloon. Further, the support element prevents the separate lumen to be squeezed close from the outside, e.g. when the catheter passes through a narrow passage or when the catheter is bend around a sharp turn.

The support element preferably is in the form of at least one strut. Said at least one strut preferably extends along the entire length of the duct, i.e. from the proximal end of the catheter to the proximal position of the balloon, preferably along a central axis of the duct. Preferably, said at least one strut comprises openings which allow an exchange of fluid trough said at least one strut, such as to allow an uniform distribution of fluid and/or pressure.

Preferably, said elongated member comprises an access opening at the end position, said access opening allowing the passage of a guidewire into and from the inner lumen. Therefore, a guide wire introduced into the inner lumen from the distal end of the catheter may exit the inner lumen at the end position. This allows the use of the catheter as so-called rapid exchange or monorail catheter. Preferably, said access opening is in the form of a slit or hole through a circumferential wall of the elongated member. Preferably, the dimensions of the access opening are selected such as to allow a guidewire with a diameter of 0.1 mm to 0.4 mm to pass therethrough.

The access opening may simply be manufactured by cutting or piercing the elongated member at the end position. As no elaborate access port is needed, the manufacturing process is greatly facilitated.

Preferably, said elongated member comprises a reinforcement member stretching from the proximal end to the end position. The reinforcement member increases the bending stiffness of the elongated member in this proximal section of the catheter extending between the proximal end and the end position. Hence, the catheter does not require a separate hypotube, as the reinforcement member serves the same function.

The reinforcement member preferably comprises a distal tip which is in the shape of a ramp pointing towards said access opening. This has the advantage that a guide wire which is introduced into the inner lumen at the distal end and which is advanced through the inner lumen will be guided towards the access opening by the ramp at the end position.

As understood herein, a "ramp" has an inclined surface or curved surface which is not symmetric relative to a length axis of the catheter. With other words, the distal tip of the reinforcement member extends further in the direction of the distal end on a first side of the inner lumen as on a second side, which is located 180° from the first side. Said second side is preferably oriented towards the access opening, so that the inclined or curved surface of the ramp guides a guide wire impinging on said surface towards the access opening.

The distal tip of the reinforcement member is preferably machined into the appropriate shape prior to the assembly of the catheter.

Preferably, the elongated member is made of a hollow tube into which the reinforcement member is introduced from the proximal end. Hence, such an elongated member may be easily manufactured out of just two parts. The elongated member may be made of a polymer or co-polymer material, a metal or a metal alloy. The elongated member is preferably provided as wire or filament which is cut to an appropriate length.

Preferably, the reinforcement member may be made of at least one polymer which is co-extruded at the same time as the tube of the elongated member. This allows to further reduce the number of parts and assembly steps required to manufacture the catheter.

In a further preferred embodiment, the reinforcement member has a stiffness which varies from the proximal end towards the end position. This allows adapting the stiffness of the proximal section of the catheter for different procedures or anatomical conditions.

Preferably, the stiffness of the reinforcement member decreases from the proximal end to the end position. This decrease is preferably constant. However, in certain embodiments, the decrease may be realized in a step-wise manner.

In order to vary the stiffness of the reinforcement member, two or more polymers each having a different stiffness may be mixed in varying ratios along the length of the reinforcement member, i.e. between the proximal end and the end position, during extrusion.

Preferably, the elongated member comprises a proximal element extending from the proximal end to the end position, said proximal element being made of solid material and serving as reinforcement member, as well as a distal element extending from the end position towards the distal end, said distal element including the inner lumen. Said proximal element and said distal element are preferably connected together, e.g. by means of welding or with an adhesive.

The distal element is preferably in the form or a hollow tube enclosing the inner lumen. The proximal element preferably is in the form of a rod. Said proximal element and said distal element may be made of the same material or of different materials. Further, said proximal element may be manufactured of a multiplicity of flexible rods twisted in a rope like manner.

A distal tip of said proximal element is preferably inserted into the inner lumen of the distal element in the area of the end position. This allows a very simple assembly of the elongated member. The connection of the proximal element to the distal element may be made by a form fit or press fit connection. Alternatively, the distal element may be shrunk wrapped onto the proximal element or both elements are welded or glued together by means of an adhesive.

In a preferred embodiment, the proximal element is made of a metal or metal alloy and the distal element is made of a polymer material. With such a configuration the proximal element has a higher stiffness as the distal element, which facilitates the insertion and pushing of the catheter trough hollow organs of a patients, specifically through arteries or veins.

The present application further relates to a method for manufacturing a catheter. In a first step, an elongated member having a proximal end and a distal end is provided. The elongated member comprises an inner lumen extending from the distal end towards the proximal end to an end position. Then an inflatable balloon is arranged over the elongated member in an area of the distal end, the balloon extending from a distal position to a proximal position. In a next step, a duct defining a separate lumen is provided and connected to the proximal end of the elongated member and to the balloon at the proximal positon. Finally, the balloon is connected to the elongated member.

Preferably, the method is used for manufacturing a catheter as described above.

Preferably, the duct is freely spirally wound around the elongated member before the connection step. This allows to keep the duct in close proximity of the elongated member, while still enabling free translation of the duct relative to the elongated member.

Preferably, the balloon is connected to the elongated member at the proximal position at the same time as the duct is connected to the balloon. This further reduces the number of assembly steps required to manufacture the catheter. Preferably, said connection is made by means of welding. In order to allow the free passage of fluid between the separate lumen and the volume of the balloon, a fluid connection between the separate lumen and the volume of the balloon must remain open. Hence, preferably, a metal wire is introduced into the separate lumen from a distal end of said duct such that the separate lumen remains open during the welding step.

Preferably, prior to the first step, the elongated member is produced by inserting a reinforcement member into a hollow tube, said reinforcement member only extending along a part of the length of said tube, wherein the part of the tube without the reinforcement member includes the inner lumen of the elongated member. Said reinforcement member is preferably connected to the hollow tube, e.g. by an adhesive or by welding. Alternatively, the hollow tube may be shrunk wrapped onto said reinforcement member.

Alternatively, prior to the first step, the elongated member is produced by assembling a proximal element made of solid material with a distal element including an inner lumen. The distal element is preferably in the form of a hollow tube encircling said inner lumen. The proximal element is preferably connected to the distal element by means of welding or by means of an adhesive. Preferably, said distal element is in the form of a rod which is inserted into the hollow tube at a proximal end of the distal element.

Other advantageous embodiments and combinations of features come out from the detailed description below and the entirety of the claims.

BRIEF DESCRIPTION OF THE DRAWINGS

The drawings used to explain the embodiments show:

FIG. 2a a cross section of the catheter in FIG. 1 in the distal section;

FIG. 2b a cross section of the catheter in FIG. 1 in the proximal section;

In the figures, the same components are given the same reference symbols.

DETAILED DESCRIPTION OF PREFERRED EMBODIMENTS

Figure 1:
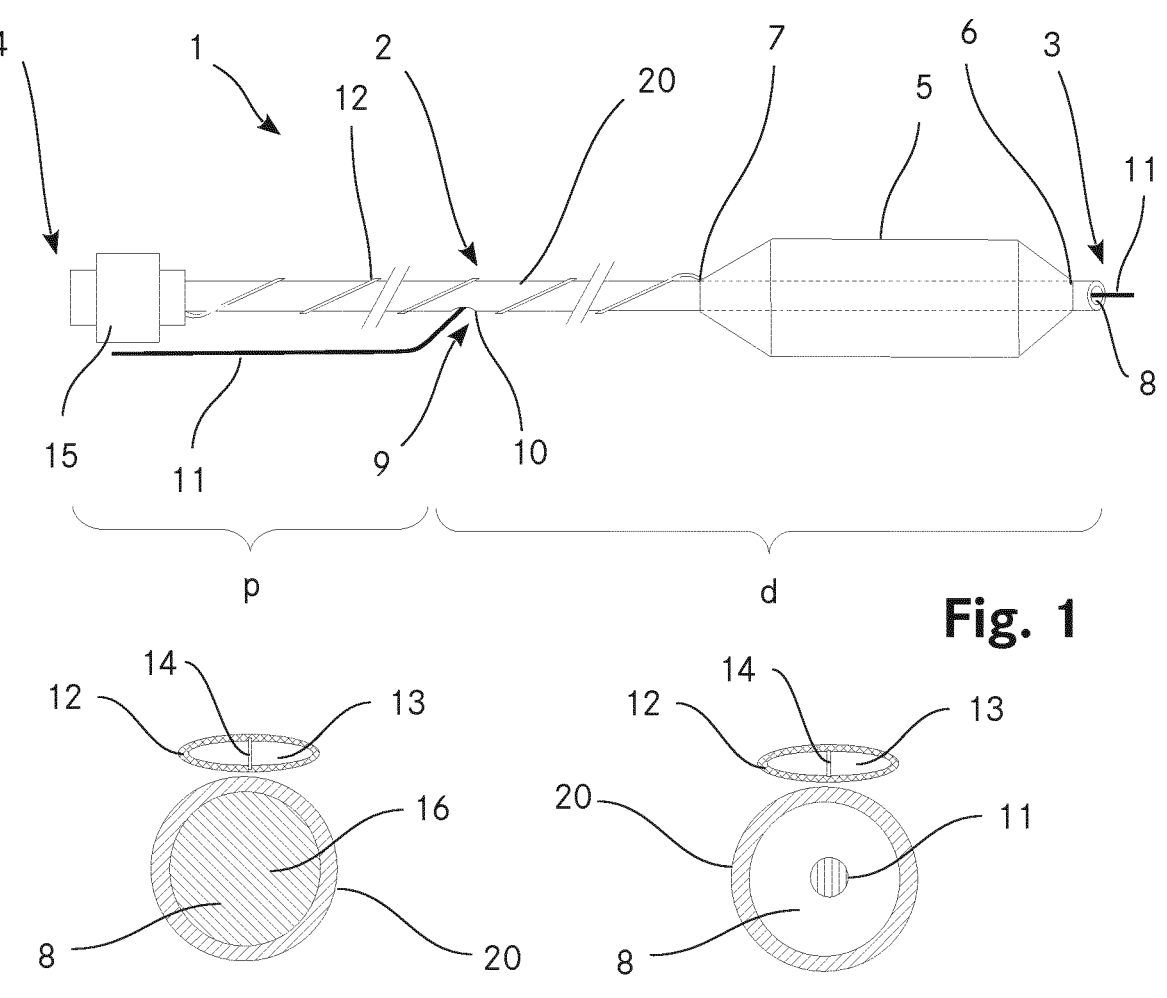
FIG. 1 a schematic drawing of a first embodiment of a catheter according to the present invention.

FIG. 1 is a schematic drawing of a first embodiment of a catheter 1 according to the present invention. The catheter 1 comprises an elongated member 2 having a distal end 3 and a proximal end 4. In the embodiment as shown in FIG. 1, the elongated member 2 is made of a hollow tube 20 of polymeric material. An inner lumen 8 stretches along a part of the length of the elongated member 2 from the distal end 3 to an end position 9. The inner lumen 8 is open at the distal end 3. This allows the introduction of a guidewire 11 into the inner lumen 8.

In the area of the distal end 3, an inflatable balloon 5 is arranged on said elongated member 2. The balloon 5 is shown in the inflated state. The balloon extends from a distal position 6 to a proximal position 7.

At the end position 9, the elongated member 2 comprises an access opening 10 which allows the passage of the guidewire 11 out or into the inner lumen 8. The end position 9 is located proximal to the proximal position 7 of the balloon 5. The combination of the inner lumen 8, which is open at the distal end 3, with the access opening 9 allows the use of the catheter 1 as so-called rapid exchange or monorail catheter. The distance between the proximal end 4 and the end position 9 defines a proximal section p of the catheter 1 while the distance between the end position 9 and the distal end 3 defines a distal section d of the catheter 1.

The catheter 1 further comprises a duct 12 which is connected to the elongated member 2 only at the proximal end 4 and at the proximal position 7. The duct 12 includes a separate lumen which is used as inflation lumen for the balloon 5. Therefore, the separate lumen is in fluid connection with a volume enclosed by the balloon 5 in the area of the proximal position 7. By means of the separate lumen a fluid may be pumped under pressure into the balloon 5 in order to inflate it. For deflating the balloon 5, the fluid is aspirated by applying an underpressure on the separate lumen. The duct 12 is spirally wound around the elongated member 2. Between the connections at the proximal end 4 and at the proximal position 7 the duct 12 is not connected to the elongated member 2, such that the duct 12 is freely movable relative to the elongated member 2.

At the proximal end 4, the catheter 1 comprises an adapter 15. By means of the adapter 15, the catheter 1 may be connected to further equipment, such as e.g. a source of fluid.

FIGS. 2a and 2b show two cross sections of the catheter 1 as shown in FIG. 1. In FIG. 2a a cross section in the distal section d of the catheter 1 is shown. The inner lumen 8 is open and comprises the guidewire 11. The cross-section of the hollow tube 20 forming the elongated member 2 is of a round shape. The duct 12 is located closely to the elongated member 2, as the duct 12 is spirally wound around elongated member 2. The duct 12 is hollow and includes the separate lumen 13. The duct 12 has a cross section in the shape of an ellipse. In order to prevent a collapse of the separate lumen 13, a support element 14 which extends longitudinally along the length of the duct 12 is arranged along a length axis of the duct 12 within the separate lumen 13. The support element connects two opposite faces of the circumferential wall of the duct and keeps those faces at a defined distance from each other.

FIG. 2b shows a cross section of the catheter 1 in the proximal section p. In the proximal section p, the elongated member 2 comprises a reinforcement member 16 which is introduced into the hollow tube 20 from the proximal end 4 and which extends from said proximal end 4 to the end position 9. The reinforcement member 16 is shaped and sized such as to completely fill the hollow tube 20.

Figure 3:
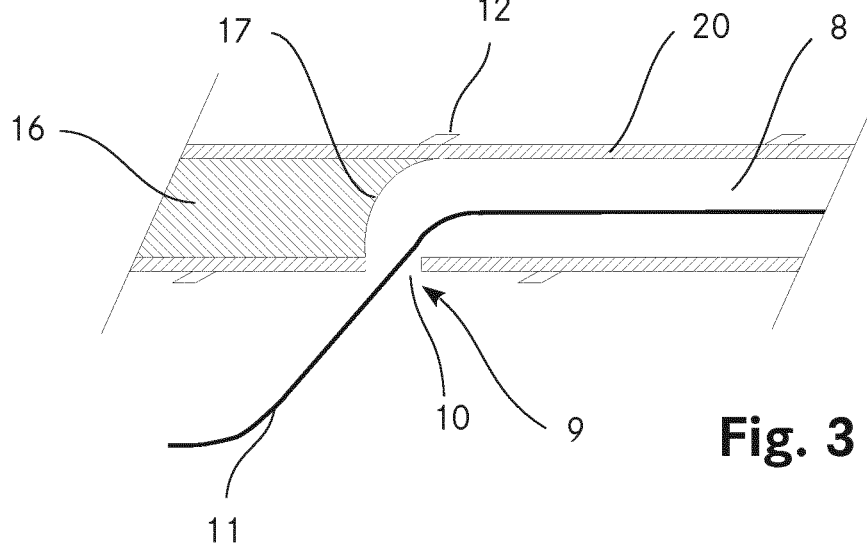
FIG. 3 a longitudinal section of the catheter according to FIG. 1 in the area of the end position.

FIG. 3 shows a longitudinal section of the catheter 1 according to FIG. 1 in the area of the end position 9. At the end position 9, the reinforcement member 16 comprises a distal tip 17 which is in the form of a ramp pointing towards the access opening 10. This configuration of the distal tip 17 guides a guidewire 11 which is introduced into the inner lumen 8 at the distal end 3 and which is subsequently pushed through the inner lumen 8 towards the proximal end 4 automatically towards the access opening 10.

Figures 4, 5:
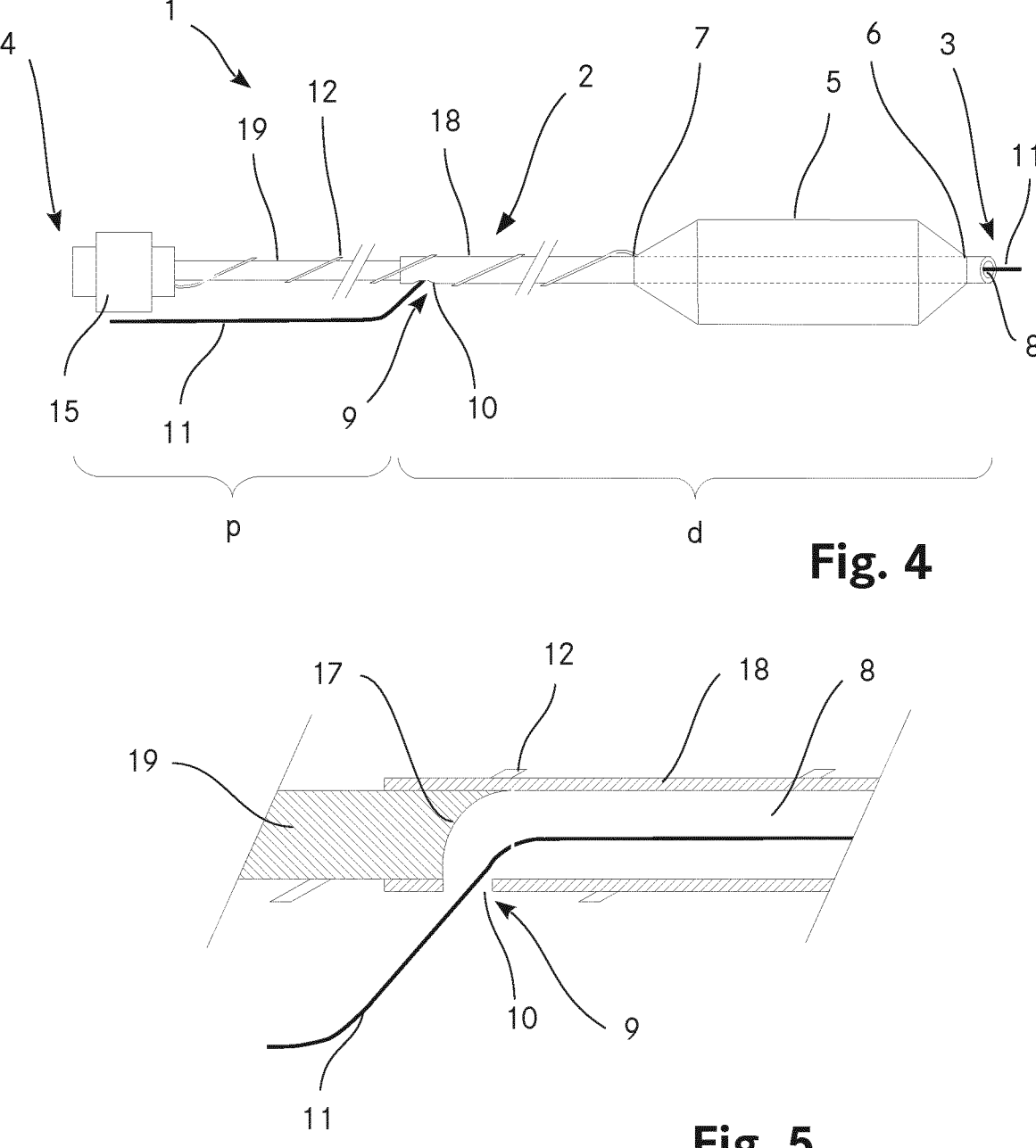
FIG. 4 a schematic drawing of a second embodiment of a catheter according to the present invention.
FIG. 5 a longitudinal section of the catheter according to FIG. 4 in the area of the end positon.

FIG. 4 is a schematic drawing of a second embodiment of a catheter 1 according to the present invention. Contrary to the first embodiment of the catheter as shown in FIG. 1, the elongated body 2 is made of a proximal element 19 extending from the proximal end 4 to the end position 9 as well as of a distal element 18 extending from the end position 9 to the distal end 3. The distal element 18 is made of a hollow tube which includes the inner lumen 8. The proximal element 19 is made of a rod of solid material. The hollow tube of the distal element 18 is preferably made of a polymeric material while the rod of solid material of the proximal element 19 is made of a wire of a metal or metal alloy. The proximal element 19 serves the function of the reinforcement member 16 in the first embodiment. The distal element 18 and the proximal element 19 are connected together in the area of the end position 9. Otherwise, the catheter 1 according to the second embodiment further comprises the same parts as the catheter 1 according to the first embodiment, namely a balloon 5, an access opening 10, an adapter 15 and a duct 12 with a separate lumen 13.

FIG. 5 shows a longitudinal section of the catheter according to the second embodiment shown in FIG. 4 in the area of the end positon 9. As may be seen, the proximal element 19 is introduced into the hollow tube of the distal element 18. Both elements are connected together by welding or by means of an adhesive. Like the reinforcement element 16 of the first embodiment, the proximal element 19 made of solid material comprises a distal tip 17 which is shaped like a ramp pointing towards the access opening 10 in order to guide the guide wire towards said access opening 10.

The invention claimed is:

1. A catheter comprising:

an elongated member having a proximal end and a distal end, and an inflatable balloon arranged on the elongated member in an area of the distal end thereof, the balloon extending from a distal position to a proximal position, wherein the elongated member comprises an inner lumen extending from the distal end to an end position proximal to the balloon and a reinforcement member stretching from the proximal end to the end position and having a distal tip in the shape of a ramp pointing towards an access opening, the inner lumen being open at the distal end, and the catheter comprises a duct connected to the proximal end and to the balloon at the proximal position, the duct defining a separate lumen to convey a fluid to and from the balloon, wherein the duct is freely spirally wound around the elongated member between the proximal end and the balloon at the proximal position.

2. The catheter according to claim 1, wherein the duct has a cross section in the form of an oval or circle.

3. The catheter according to claim 2, wherein the cross section is an ellipse.

4. The catheter according to claim 1, wherein the duct comprises at least one support element arranged longitudinally along a length of the duct within the separate lumen.

5. The catheter according to claim 1, wherein the elongated member includes the access opening at the end position, the access opening allowing the passage of a guidewire into and from the inner lumen.

6. The catheter according to claim 1, wherein the elongated member is made of a hollow tube into which the reinforcement member is introduced from the proximal end to the end position.

7. The catheter according to claim 1, wherein the elongated member comprises:

a proximal element extending from the proximal end to the end position, the proximal element being made of solid material and serving as the reinforcement member, and a distal element extending from the end position towards the distal end, the distal element including the inner lumen.

8. The catheter according to claim 7, wherein a distal tip of the proximal element is inserted into the inner lumen of the distal element in the area of the end position.

9. The catheter according to claim 7, wherein:

the proximal element is made of a metal or metal alloy and the distal element is made of a polymer material.

10. The catheter according to claim 1, wherein the duct is freely spirally wound around the elongated member from where the duct is connected to the proximal end.

11. A catheter comprising:

an elongated member having a proximal end and a distal end, and an inflatable balloon arranged on the elongated member in an area of the distal end thereof, the balloon extending from a distal position to a proximal position, wherein the elongated member comprises a proximal element extending from the proximal end to an end position, a distal element extending from the end position towards the distal end, and an inner lumen extending from the distal end to the end position proximal to the balloon, the proximal element being made of solid material and serving as a reinforcement member, the distal element including the inner lumen, and the inner lumen being open at the distal end, wherein a distal tip of the proximal element is inserted into the inner lumen of the distal element in the area of the end position, and the catheter comprises a duct connected to the proximal end and to the balloon at the proximal position, the duct defining a separate lumen to convey a fluid to and from the balloon, wherein the duct is freely spirally wound around the elongated member up to where the duct is connected to the balloon at the proximal position.

12. The catheter according to claim 11, wherein the duct has a cross section in the form of an oval or circle.

13. The catheter according to claim 11, wherein the duct comprises at least one support element arranged longitudinally along a length of the duct within the separate lumen.

14. The catheter according to claim 11, wherein the elongated member includes an access opening at the end position, the access opening allowing the passage of a guidewire into and from the inner lumen.

15. The catheter according to claim 11, wherein:

the proximal element is made of a metal or metal alloy and the distal element is made of a polymer material.

16. A method for manufacturing a catheter, comprising:

a) providing an elongated member having a proximal end and a distal end, the elongated member comprising an inner lumen extending from the distal end towards the proximal end to an end position distal to the proximal end and a reinforcement member stretching from the proximal end to the end position and having a distal tip in the shape of a ramp pointing towards an access opening;

b) arranging an inflatable balloon over the elongated member in an area of the distal end, the balloon extending from a distal position to a proximal position, the end position of the elongated member being located between the proximal end of the elongated member and the proximal position of the balloon;

c) providing a duct, the duct defining a separate lumen;

d) connecting the duct to the proximal end of the elongated member and to the balloon at the proximal position, such that the duct is freely and spirally wound around the elongated member up to where the duct is connected to the balloon at the proximal position; and e) connecting the balloon to the elongated member.

17. A method according to claim 16, wherein the balloon is connected to the elongated member at the proximal position at the same time that the duct is connected to the balloon.

18. A method according to claim 16, wherein:

prior to step a), the elongated member is produced by inserting the reinforcement member into a tube spanning from the proximal end to the distal end, the reinforcement member only extending along a part of a length of the tube, and the part of the tube without the reinforcement member constitutes the inner lumen of the elongated member.

19. A method according to claim 16, wherein prior to step a), the elongated member is produced by assembling a proximal element made of solid material with a distal element that includes the inner lumen.

20. A method according to claim 16, wherein the duct is freely spirally wound around the elongated member from where the duct is connected to the proximal end.

* * * * *